(12) United States Patent
Hsing et al.

(10) Patent No.: US 8,465,926 B2
(45) Date of Patent: Jun. 18, 2013

(54) METHOD AND SYSTEM FOR REAL TIME QUANTIFICATION AND MONITORING OF NUCLEIC ACID AMPLIFICATION USING ELECTROCONDUCTIVE OR ELECTROCHEMICALLY ACTIVE LABELS

(75) Inventors: I Ming Hsing, Kowloon (CN); Thomas Ming Hung Lee, Hong Kong (CN); Stephen Siu Wai Yeung, Shatin (CN)

(73) Assignee: The Hong Kong University of Science and Technology, Hong Kong SAR (CN)

( * ) Notice: Subject to any disclaimer, the term of this patent is extended or adjusted under 35 U.S.C. 154(b) by 408 days.

(21) Appl. No.: 12/377,124

(22) PCT Filed: Aug. 10, 2007

(86) PCT No.: PCT/CN2007/002395
§ 371 (c)(1),
(2), (4) Date: Feb. 11, 2009

(87) PCT Pub. No.: WO2008/022538
PCT Pub. Date: Feb. 28, 2008

(65) Prior Publication Data
US 2010/0184028 A1     Jul. 22, 2010

Related U.S. Application Data

(60) Provisional application No. 60/836,990, filed on Aug. 11, 2006.

(51) Int. Cl.
*C12Q 1/68* (2006.01)
*C12P 19/34* (2006.01)

(52) U.S. Cl.
USPC .................................. 435/6.12; 435/91.2

(58) Field of Classification Search
USPC ...................................... 435/6, 91.2
See application file for complete search history.

(56) References Cited

U.S. PATENT DOCUMENTS

| | | | | |
|---|---|---|---|---|
| 6,127,127 | A * | 10/2000 | Eckhardt et al. | 435/6 |
| 7,371,530 | B2 * | 5/2008 | Han et al. | 435/6 |
| 7,393,644 | B2 * | 7/2008 | Lee et al. | 435/6 |
| 2004/0152097 | A1 * | 8/2004 | Takenaka | 435/6 |
| 2005/0214759 | A1 * | 9/2005 | Wlassof et al. | 435/6 |

OTHER PUBLICATIONS

Wilhelm et al, Real-Time Polymerase Chain Reaction, ChemBioChem, 2003, 4, 1120-1128.
Drummond et al, Electrochemical DNA sensors, Nature Biotechnology, 2003, 21(10), 1192-1199.
Kerman et al, Recent trends in electrochemical DNA biosensor technology, Measurement Science and Technology, 2004, 15, R1-R11.
Gooding, Electrochemical DNA Hybridization Biosensors, Electroanalysis, 2002, 14(17), 1149-1156.
Wang, Electrochemical nucleic acid biosensors, Analytica Chimica Acta, 2002, 469, 63-71.
Lai et al, Rapid, sequence-specific detection of unpurified PCR amplicons via a reusable, electrochemical sensor, PNAS, 2006, 103(11), 4017-4021.
Lee et al, Sequence-Specific Electrochemical Detection of Asymmetric PCR Amplicons of Traditional Chinese Medicinal Plant DNA, Anal. Chem., 2002, 74(19), 5057-5062.
Lee et al, Microfabricated PCR-electrochemical device for simultaneous DNA amplification and detection, Lab Chip, 2003, 3, 100-105.
Liu et al, Self-Contained, Fully Integrated Biochip for Sample Preparation, Polymerase Chain Reaction Amplification, and DNA Microarray Detection, Anal. Chem., 2004, 76(7), 1824-1831.
Adessi et al, Solid phase DNA amplification: characterisation of primer attachment and amplification mechanisms, Nucleic Acids Research, 2000, 28(20), e87.
Carmon et al, Solid-Phase PCR in Microwells: Effects of Linker Length and Composition on Tethering, Hybridization, and Extension, BioTechniques, 2002, 32(2), 410-420.
Higuchi et al, Simultaneous amplification and detection of specific DNA sequences, Biotechnology, 1992, 10, 413-417.
Heid et al, Real Time Quantitative PCR, Genome Research, 1996, 6, 986-994.
Tyagi et al, Molecular Beacons: Probes that Fluoresce upon Hybridization, Nature Biotechnology, 1996, 14, 303-308.
Wlassoff et al, Ferrocene conjugates of dUTP for enzymatic redox labelling of DNA, Nucleic Acids Research, 2002, 30(12), e58.
Yeung et al, A DNA biochip for on-the-spot multiplexed pathogen identification, Nucleic Acids Research, 2006, 34 (18), e118.
Yeung et al, Electrochemical Real-Time Polymerase Chain Reaction, J. Am. Chem. Soc., 2006, 128(41), 13374-13375.

* cited by examiner

*Primary Examiner* — Kenneth Horlick
(74) *Attorney, Agent, or Firm* — Eagle IP Limited; Jacqueline C. Lui

(57) ABSTRACT

A method and device for real time electrochemically or electrically monitoring and detecting nucleic acid amplification products, i.e. after each polymerase chain reaction cycle, utilizes electrochemically active or electrically conductive reporter materials. An electric voltage is applied and electric signals are measured during a PCR amplification process to the electrodes that is suitable for quantifying the amplified products of a sample's nucleic acid(s) produced. This technique is suitable for point-of-use applications, e.g. detecting bioanalytes in remote locations.

7 Claims, 12 Drawing Sheets

METHOD AND SYSTEM FOR REAL TIME QUANTIFICATION AND MONITORING OF NUCLEIC ACID AMPLIFICATION USING ELECTROCONDUCTIVE OR ELECTROCHEMICALLY ACTIVE LABELS

CROSS-REFERENCE TO RELATED APPLICATION

This application claims benefit under 35 U.S.C. §119(e) of U.S. Provisional Application having Ser. No. 60/836,990 filed 11 Aug. 2006, which is hereby incorporated by reference herein in its entirety.

REFERENCE TO SEQUENCE LISTING

The hard copy of the sequence listing submitted herewith and the corresponding computer readable form are both incorporated herein by reference in their entireties.

FIELD OF THE INVENTION

The present invention relates to a novel and unobvious method for detecting and quantifying nucleic acids and nucleic acid-coupled molecules comprising the real time electrochemical detection by a polymerase chain reaction (PCR) of nucleic acids or nucleic acid coupled molecules, where the electrochemical or electrically conductive label attaches itself to the target nucleic acid during the PCR facilitated amplification step.

DESCRIPTION OF THE BACKGROUND

Nucleic acid analysis has played an important role for the detection of pathogens and genetic diseases. In recent years, its usefulness has been seen in many decentralized applications such as point-of-care diagnostics, environmental and food monitoring, and the detection of biological warfare agents. Among the available analytical techniques for DNA analyses, real-time polymerase chain reaction has been a key technology for high-speed testing and accurate quantification.

Various assays based on real-time PCR have been developed utilizing fluorescence-linked reporters such as SYBR Green 1, hydrolysis probe, and hybridization probes for simultaneous deoxyribonucleic acid (DNA) amplification and PCR amplicon detection. Despite wide acceptance, their use is largely limited in clinical and research laboratory settings. The difficulty in advancing this technology for point-of-care testing (POCT) applications lies in the requirement of bulky and complex optical systems for the DNA amplicon detection. The goal of performing complete DNA analyses with a hand-held instrument is not attainable based on optical detection systems that are bulky and cumbersome. A far more suitable alternative for this type of use and one that is extremely suited for POCT, is a system based on the detection of electrochemical signals.

Over the past years, numerous studies have been carried out on electrochemical DNA sensors, some of which focused on PCR amplicon detection. Efforts have also been made in developing DNA microchips having an attached electrochemical signaling label employed in conjunction with an electrochemical detection system for post-PCR product identification. The latter prior art post-PCR hybridization-based platform suffers from a long assay time and has a narrow dynamic range when compared to fluorescence-based real-time PCR methods.

In view thereof, there is a need for developing a method for detecting and quantifying nucleic acid(s) in a sample that is accurate, reproducible, and safe and, at the same time, may be performed in small scale devices.

SUMMARY OF THE INVENTION

Figure 1:
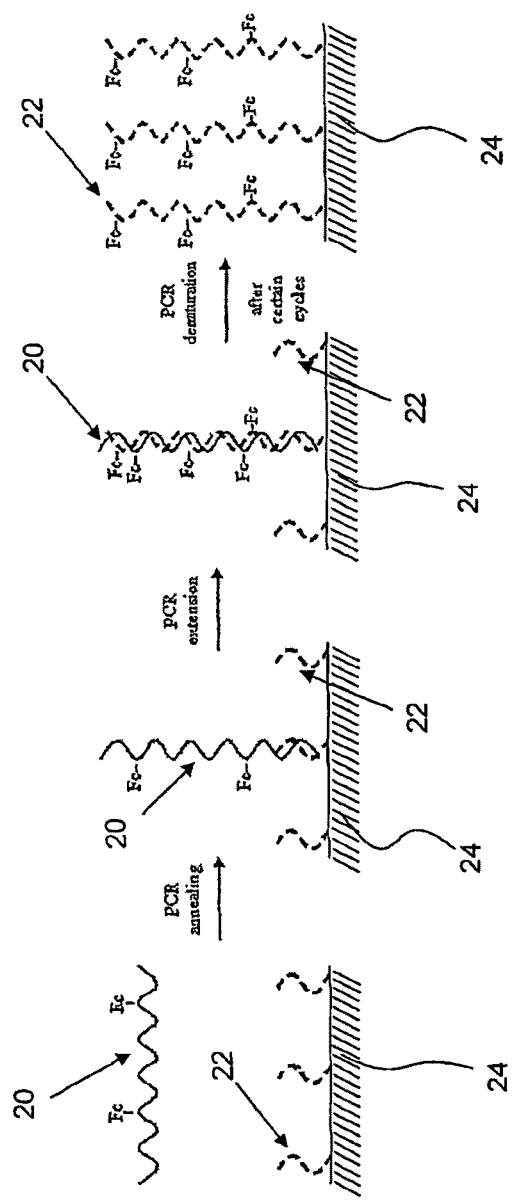
FIG. 1 shows a scheme of a solid-phase method employing a red-ox probe according to one embodiment of the present invention.

In light of the foregoing background, it is an object of the present invention to provide a method for the detection and quantification of nucleic acid(s) or nucleic acid coupled molecules in a sample and a system thereof.

Accordingly, the present invention, in one aspect, is a real time solid phase method for electrochemically or electrically monitoring or quantifying the amount of nucleic acid(s) by formation of a polymerase chain reaction (PCR) produced polynucleic acid(s), that comprises the following steps:

contacting a sample comprising a target nucleic acid(s), a solid surface bound probe(s) comprising a first primer(s) provided with a sequence(s) that is (are) complementary to at least a portion of one end of the target nucleic acid(s), a second primer(s) in solution that is (are) complementary to at least a portion of the opposing end of the complementary strand of the target nucleic acid(s), and an electrochemically or electrically conductive marker(s) that is (are) adapted for incorporation into a polynucleic acid(s) by chain polymerization and when incorporated thereof produces a signal(s) change(s) if subjected to an electric potential;

adding a polymerase chain reaction enzyme(s) under conditions effective for PCR amplification to occur;

applying an electric potential to the sample and detecting or measuring in real time the electric signal(s) produced by the labeled marker(s) incorporated into the solid surface bound probes; and quantifying the amount of nucleic acid(s) present in the sample and the amount of polynucleic acid(s) produced by correlating the change(s) in signal(s) over time with the formation of polynucleic acid(s).

Another aspect of the present invention provides a real time solution phase method for electrochemically or electrically monitoring or quantifying the amount of nucleic acid(s) by formation of a polymerase chain reaction (PCR) produced polynucleic acid(s), that comprises the following steps:

contacting a sample comprising a target nucleic acid(s), a probe(s) having an electrical charge(s) neutral or positive that is complementary to at least a portion of the target nucleic acid(s) and is only attracted to an electrode surface when hybridized into the target nucleic acid(s), and an electrochemically or electrically conductive labeled marker(s) that is (are) operatively linked to the probe(s) and that when incorporated into the target nucleic acid(s) upon hybridization and subjected to an electric potential produces an intensity change;

applying an electric potential to the sample and detecting or measuring in real time the electric signal produced by the labeled marker(s) incorporated into the target nucleic acid(s); and quantifying the amount of nucleic acid(s) present in the sample and the amount of polynucleic acid(s) produced by correlating the change(s) in signal(s) over time with the formation of polynucleic acid(s).

In a further aspect of the present invention, a microchip is provided, and comprises an electrochemically or electrically conductive electrode, and a solid support adapted to receive a molecule comprising a nucleic acid(s) wherein the microchip is adapted to be used for the solid phase or solution phase method as described above. In a preferred embodiment, the electrode is provided with a surface comprising a solid support; in a more preferred embodiment, the solid support comprises glass, and the surface of at least one electrode(s), being patterned and integrated into the microchip, comprise(s) indium tin oxide, gold, or platinum.

In another preferred embodiment, the microchip further comprises a temperature sensor(s) and a micro heater(s) integrated therein.

Yet another aspect of the present invention provides a device for measuring electrochemical or electric signals, comprising the microchip of this invention. In a preferred embodiment, the device is a portable device and/or a microdevice.

In another aspect of the present invention, an electrochemical signal detection kit is provided comprising PCR primers and the microchip(s) of this invention; in a more preferred embodiment, the kit further comprises PCR reagents other than primers, and the like.

There are many advantages of the present invention. For instance, since the detection and/or quantification of nucleic acid amplification product is performed in real time during the PCR reaction, it is important to note that the method and system according to this invention are thermally stable, having a negligible inhibitory effect on the PCR reaction. Also, this method is accurate, reproducible, and safe, even in the absence of an additional step of washing off of unreacted molecules, especially the soluble and non-incorporated labeled molecules and markers employed in the reaction.

In addition, since the method may be performed in small scale point-of-care devices, it may be integrated into handheld instruments for point-of-care DNA analysis. This provides a significant contribution to the medical diagnostics industry as well as to environmental monitoring for decentralized applications.

When compared to optically-based devices, the present invention provides a technology that results in significantly reduced expenses; more particularly, this method may be employed in miniaturized devices, e.g. a portable real time PCR analyzer, which is currently unavailable in the market place. Moreover, although the required starting concentration of target nucleic acid analyte is somewhat higher than that required by optically-based methods, the electrochemistry-based real-time PCR method of this invention is very sensitive, with an onset of about 3 PCR cycles.

DESCRIPTION OF THE PREFERRED EMBODIMENTS

This invention arose from the desire by the inventors to improve on prior art technology and, at the same time, overcome the cumbersome and expensive type of hardware that are currently required in the art. This invention aims to address the deficiencies inherent in the currently employed optically, e.g. fluorescence-based PCR methods that are standard in the industry, and is an improvement over the real time detection method employing an electrochemical label attached to the solid substrate.

During the course of their investigations, the inventors endeavored to discover a simpler, less expensive, and generally superior device and method for detection and quantification of nucleic acids. The inventors came into the realization that of many alternatives tested, the PCR reaction conditions were best suited for being coupled to a detection system based on electrochemical/electrical signals. Moreover, by coupling this detection method to a PCR reaction with appropriate electrochemical or electrically conductive reporter(s), amplicon(s) or probe(s), where the electrochemical label would be incorporated into the amplified nucleic acid, they would be able to provide a superior method of detection and quantification of target macromolecules, such as nucleic acids or nucleic acid coupled molecules, that is less costly, simpler and more accurate than prior art methods.

DEFINITIONS

As used herein and in the claims, a "sample" refers to a sample of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

The terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 6 nucleotides, preferably at least about 10-12 nucleotides, and more preferably at least about 15-20 nucleotides corresponding to a region of the designated nucleotide sequence. "Corresponding" means identical to or complementary to the designated sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

The term "peptide nucleic acid (PNA)" refers to an artificially synthesized chemical having a structure resembling DNA or RNA, in which the backbone of PNA is composed of repeating N-(2-aminoethyl)-glycine units linked by peptide bonds such that various purine and pyrimidine bases can be linked to the backbone by methylene carbonyl bonds. By virtue of this structure, PNA is electrically neutral.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein and in the claims, the term "target nucleic acid", "target sequence" or "target nucleic acid sequence" refers to a region of the oligonucleotide which is to be either amplified, detected or both. The target sequence resides between the two primer sequences used for amplification.

The term "probe" refers to a labeled oligonucleotide which forms a duplex structure with a sequence in the target nucleic acid, due to complementarity of at least one sequence in the probe with a sequence in the target region. Specifically for the solid phase method, once all the probes are attached onto the electrode surface, all the remaining active sites on the electrode surface may be "blocked" to restrict the incorporation of unbound or unreacted labeled markers into the electrode surface.

The term "label" as used herein and in the claims refers to any atom or molecule which can be used to provide a detectable (preferably quantifiable) signal, and which can be attached to a nucleic acid or protein.

By "adjacent" refers to the positioning of the primer with respect to the probe on its complementary strand of the template nucleic acid. The primer and probe may be separated by 1 to about 20 nucleotides, more preferably, about 1 to 10 nucleotides, or may directly abut one another, as may be desirable for detection with a polymerization-independent process. Alternatively, for use in PCR amplification and detection methods as taught herein, the "adjacency" may be anywhere within the sequence to be amplified.

As used herein and in the claims, "operatively linked", "bound" or "coupled", in a broad sense, refers to the association between molecules or a molecule and a substrate's surface and include, among others, either a direct or indirect (covalent or ionic) linking therebetween. For ease of description, the term "bound" is generally used to refer to the association between a molecule and a solid surface, whereas "coupled" generally refers to the association between two molecules. The phrase "operatively linked" includes all types of linkages, whether ionic or covalent, molecule to molecule or molecule to surface. The term "electrochemically or electrically conductive labeled markers", as used herein, refers to markers coupled to electrochemical or electrically conductive molecule.

The term "ferrocene derivatives" refer to chemical compounds having two cyclopentadienyl rings bound on opposite sides of a central metal atom, such as iron, in a sandwich structure.

The Invention

General Method

The practice of the present invention employs, unless otherwise indicated, conventional techniques of molecular biology, which are within the skill of the art. Such techniques are explained fully in the literature. See, e.g., Sambrook, Frtisch & Maniatis, Molecular Cloning; A Laboratory Manual, Second Edition (1989); Oligonucleotide Synthesis (M. J. Gait, ed., 1984); and Nucleic Acid Hybridization (B. D Hames & S. J. Higgins, eds., 1984). All patents, patent applications, and publications mentioned herein, both supra and infra, are hereby incorporated by reference.

The reagents employed in the methods of the invention may be packaged into diagnostic kits. Diagnostic kits include the labeled marker(s) and the primers in separate containers. If the marker is unlabeled, the specific labeling reagents may also be included in the kit. The kit may also contain other suitably packaged reagents and materials needed for amplification, for example, buffers, dNTPs, and/or polymerizing means, and for detection analysis, for example, enzymes and solid phase extractants, as well as instructions for conducting the assay.

As a result of their work, the inventors discovered a novel and unobvious electrochemical real-time PCR (ERT-PCR) technique employing a solid support, e.g. silicon glass microchip, method for simultaneous DNA amplification and detection. This on-chip ERT-PCR process relies on the extension of oligonucleotides in either solution- and/or solid-phase(s) and the measurement of electrochemical, e.g. continuous or intermittent, signals in the presence of PCR reagents and enzymes. In one preferred implementation of the method of this invention, other parameters were adapted, including the passivation of electrode surfaces, and the mode of electrochemical scanning during the PCR process. During the course of their research, the inventors also found that the ERT-PCR's onset of the thermal cycle (about 3-5 cycles) where the analytical signal begins to be distinguishable from the background is much shorter than that of the fluorescence-based methods when employed for high template DNA detection ($3\times10^6$ copies/$\mu$L). By discovering the power of carefully controlling the concentrations of immobilized probe(s) and the polymerase enzyme, the inventors have made a critical improvement by reducing the initial template concentration of the on-chip ERT-PCR. One of the implementations of the ERT-PCR based method provided in this patent, preferably employs a microchip platform, optionally an electrode/microchip acting as a solid phase for the attachment of DNAs, that will become the standard in the industry for rapid DNA detection for POCT applications.

The present invention, thus, relates to a novel and unobvious electrochemical or electron-based method for detecting and quantifying a target molecule(s) comprising a nucleic acid(s) and/or nucleic acid coupled molecule(s) comprising a polymerase chain reaction (PCR) procedure conducted so that the target molecule(s) is (are) placed in contact with an electrochemical and/or electrically conductive reporter(s) that is (are) annealed to the target molecule(s) in the presence of a conductive electrode surface, whereby upon PCR cycling the amplification of the target molecule(s) is measured by electrochemical detection. In one preferred implementation the method comprises a real time method. This invention addresses the deficiencies inherent in the prior art of optically, e.g. fluorescence, based real-time PCR method. It does this by utilizing a novel and unobvious strategy based on the combination of a redox-labeled reporter(s), amplicon(s) or probe(s), such as a nucleic acid(s) or nucleic acid coupled molecule(s), e.g. a probe comprising a peptide coupled to a peptide nucleic acid, and conducting the PCR reaction in the presence of an electrode capable of detecting the electrochemical signal emitted by the probe(s). In another preferred embodiment, the method and apparatus are suited for conducting the PCR reaction with the red-ox probe(s) on a solid phase, e.g. an electrode. This permits the electrochemical detection of the capture of the probe with redox markers by the PCR extended oligonucleotide(s) bound to the solid phase. In yet another preferred embodiment, the reaction is detected in real time.

The inventors have developed a novel and unobvious technology suitable principally for use in two types of electrochemistry-based real time PCR devices or instruments. The first is suitably a bench-top type, which will provide superior performance to currently available real-time instruments QPCR produced by, e.g. Applied Biosystem (ABI), Stratagene and Roche. Hospitals, research/testing/teaching laboratories, government lab for food/drug testing, among others require real time PCR instruments. The second type of instrument is a portable real-time PCR analyzer, a smaller, possibly handheld, device that permits the decentralized analysis of nucleic acid samples, such as those containing pathogens and the like. The followings are other applications for the method and device of this invention, including clinical diagnostics and scientific research uses. The portable real-time PCR analyzer provides a nucleic acid biosensor for decentralized and point-of-care testing including for genetic diseases analysis, viral quantification, pathogen identification, environmental monitoring, and drug monitoring, among many others.

Thus, this invention may also preferably be practiced by employing a microchip platform strategy. That is, the electrochemical detection of the red-ox marker probe binding to the amplified nucleic acid(s) may be carried out on a portable chip based system, and even more preferably in real time. This electrochemical apparatus and method employ simple and small size, e.g. miniature instrumentation that favorably compares to the bulky and sophisticated optics required in the fluorescence-based schemes. This invention may be used for the real-time detection of bioanalyte(s), e.g. water pathogens, such as *E. Coli*, in a decentralized environment.

In another aspect of the invention, the inventors have demonstrated for the first time that the extension of an electrode-bound oligonucleotide probe, for example with a labeled marker, e.g. deoxythymine triphosphate (dTTP) substituted by ferrocene-labeled deoxyuridine triphosphate (Fc-dUTP), may be utilized to monitor DNA amplification in real-time. Briefly, an oligonucleotide probe specific to a PCR target nucleic acid or amplicon was immobilized onto an electrode, e.g. an Indium Tin Oxide (ITO) electrode. The electrode was then dipped into a PCR solution in a conventional PCR tube format and denaturation was started to separate the strands of the target nucleic acid. During the subsequent annealing step, the heat-denatured, single-stranded target nucleic acid or amplicon hybridized to the probe bound to the ITO electrode. The probe was then extended by addition of polymerase enzyme in a solid-phase PCR producing a progressive accumulation of the redox marker, now captured in the extended DNA molecule coupled to the amplicon or target nucleic acid, onto the electrode surface. During the course of various experiments, multiple samples were run in parallel under identical conditions. The electrochemical or electric signal of the marker incorporated into the electrode bound amplified DNA, e.g. ferrocene signal, was then electrochemically measured.

In addition, the inventors investigated the effect on the electrochemical detection method of the invention of passivating the electrode surface, and the electrochemical scanning during the PCR amplification that greatly affect its performance. The ability to conduct real-time PCR in a microchip is critical to its practical application to a portable device for POCT applications. The inventors' approach minimizes background noise while at the same time enhances the electrochemical signal, particularly in a microchip format.

An underlying principle of this invention is an electrochemistry-based real-time PCR method involving the use of 1) a solid-phase extension of captured nucleic acid probes on a conductive electrode surface; 2) the incorporation of more and more electrochemical or electrically conductive reporters to the amplified nucleic acid bases as the number of PCR cycles increases, and 3) the integration of electrochemical detection and nucleic acid amplification on a micro-chip platform.

Solid-Phase Extension Method

The electrical or electrochemical (EC) real-time PCR method of the invention is based on the solid-phase extension of the capture probe (in broken lines of FIG. 1) 22 with a labeled marker(s) such as, for example Fc-dUTP, Fc-dATP, Fc-dGTP or Fc-dCTP, among other electrically conductive molecules, as is schematically shown in FIG. 1. During the PCR denaturation step (preferably at about 95° C.), the double-stranded amplicon is denatured into a single-stranded form 20 (in solid lines of FIG. 1). At the annealing temperature (55° C.), the amplicon 20 hybridizes with the immobilized extension probe 22 in addition to the solution hybridization between the amplicon 20 and primers. Thereafter, the probe 22 is extended with the incorporation of Fc-dUTP by the polymerase. With this strategy, the redox signal, in proportion to the amount of amplicon, gradually builds up. The most prominent feature is the possibility to directly detect the electrochemical signal of the amplicon cycle-by-cycle. FIG.

Figure 2A:
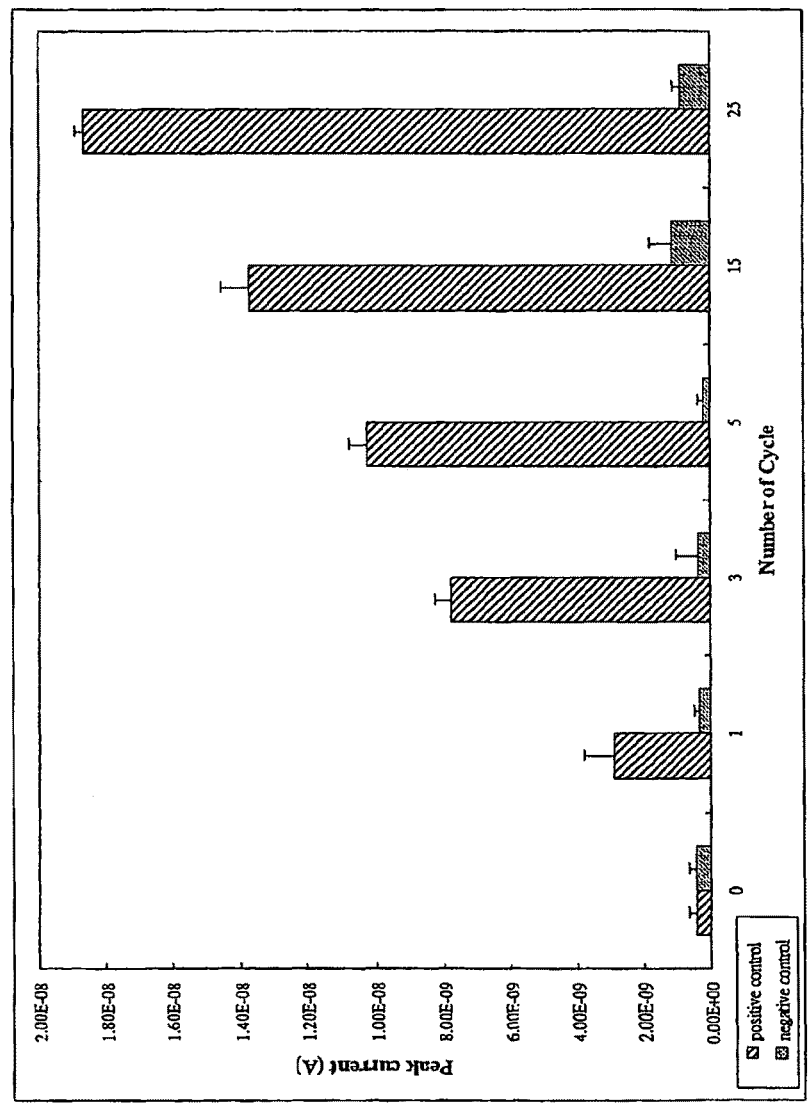
FIG. 2A provides a graph showing differential pulse signals of ferrocene at different PCR cycle numbers according to the same embodiment of the present invention.
Figure 2B:
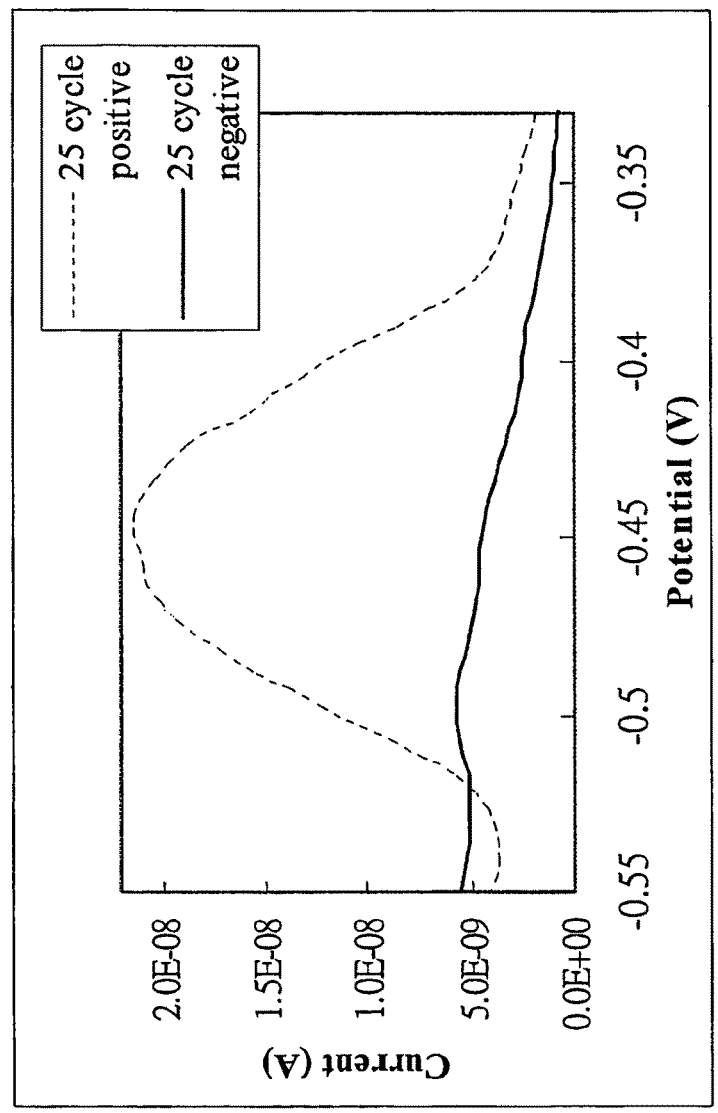
FIG. 2B shows a differential pulse voltammetric scan of the indium tin oxide (ITO) electrodes after 25-cycle PCR with (positive, broken line) or without (negative, solid line) the target template.

2A shows the differential pulse voltammetric scan of the ITO electrodes after running different PCR cycles. The electrochemical signal from the incorporated Fc increases with the PCR cycle number. Control experiments, which either do not have the template or have nonspecific template, were studied to confirm that the detected electrochemical signal indeed originated from the specific extension of the immobilized probe, and the results were shown in FIG. 2B. A close-to-flat line signal was obtained for the negative control after 25 cycles. It should be noted that, at a starting template amount similar to the prior art optical based real time PCR, the onset spot (i.e., the point at which the signal is distinguishable from the baseline) for this EC scheme occurs earlier than that for the optical one (usually at 15 to 20 cycles). This is particularly attractive for ultra-fast DNA identification in point-of-care applications.

More particularly, the present invention provides a real time solid phase method for electrochemically or electrically monitoring or quantifying the amount of nucleic acid(s) in a biological sample by formation of a polymerase chain reaction (PCR) produced polynucleic acid(s), that comprises the steps of:

contacting a sample comprising a target nucleic acid(s) ends, a solid surface bound probe(s) comprising a first primer(s) provided with a sequence(s) that is complementary to at least a portion of one end of the target nucleic acid(s), a second primer(s) in solution that is (are) complementary to at least a portion of the opposing end of the target nucleic acid(s), and an electrochemically or electrically conductive marker(s) that is (are) adapted for incorporation into a polynucleic acid(s) by chain polymerization and when incorporated thereof produces a signal(s) change(s) if subjected to an electric potential;

adding a polymerase chain reaction enzyme(s) under conditions effective for PCR amplification to occur;

applying an electric potential to the sample and detecting or measuring in real time the electric signal(s) produced by the labeled marker(s) incorporated into the solid surface bound probe(s); and quantifying the amount of nucleic acid(s) present in the sample and the amount of polynucleic acid(s) produced by correlating the change(s) in signal(s) over time with the formation of polynucleic acid(s).

In a preferred implementation, the first primer(s) is (are) immobilized onto the solid surface. In a more preferred implementation, the method provided by the present inventors may also include a step of denaturing the target nucleic acid(s) prior to polymerization, and preferably the PCR step is conducted with a PCR enzyme that is thermo-stable.

In another preferred implementation, the signal(s) change may comprise a change of current intensity, which in all likelihood will be proportional to the concentration of the polynucleic acid(s) produced and of nucleic acid(s) in the sample.

This method may be employed by running more than one PCR amplification cycle. Clearly, in this mode of the method each signal change is associated with or proportional to the amount of polynucleic acid(s) formed in each PCR amplification cycle. In yet another preferred implementation, the electric signal may be detected and/or its value measured with at least a pair of conductive electrodes placed in the sample. Multiple pairs of electrodes may also be employed as described herein.

In one preferred implementation, the surface of at least one of the conductive electrode(s) comprises indium tin oxide, gold, platinum, carbon or magnetic particles.

In an even more preferred implementation, probes may be bound onto the conductive electrode surface. In this type of method, the labels may comprise ferrocene and ferrocene derivatives, as well as others that an artisan would recognize.

In another preferred implementation, examples of markers are dUTP, dATP, dGTP, or dCTP, as well as others that are capable of accepting an electrochemical label and are suitable for incorporation in DNA amplification by PCR.

Also provided by this patent is a microchip that in its simple form comprises an electrochemically or electrically conductive electrode; and a solid support adapted to receive a molecule comprising a nucleic acid(s) wherein the microchip is adapted to be used for the solid-phase extension method as described above. The nucleic acids may be added to the solid support at the laboratory end, or the substrates may be purchased already having coupled thereto a specific probe, as desired. Laboratory techniques for attaching DNA to a solid support as well as suitable materials for the support are known in the art and need not be described in details herein. An example of solid support material is glass. In another embodiment, the microchip has an electrode that is provided with a surface comprising the solid support; that is the electrode itself is adapted for receiving the DNA. The microchip may also have integrated therein for monitoring the PCR amplification a temperature sensor(s) comprising or being formed of a metal, and a micro heater(s). The temperature sensor(s) is typically formed of or comprises platinum. However, other metals such as gold and copper, and materials exhibiting the function of temperature monitoring are also suitable. In terms of the electrodes provided with the device and/or for the microchip, the surface of at least one of them is typically formed of or comprises indium tin oxide, but other metals such as gold and platinum, or other electrically conductive materials can also be used. The electrode or a surface thereof may be patterned and integrated into the microchip.

Yet another embodiment of the invention further provides a microchip, that comprises a glass substrate wherein an electrochemically or electrically conductive electrode(s) is (are) patterned; and a silicon chip wherein a temperature sensor(s) and a micro heater(s) are integrated. In this embodiment, the silicon chip is adapted to be bonded with the glass substrate in a way to create a mircochamber therebetween such that the polymerase chain reaction (PCR) is carried out and monitored within the microchamber.

In a further embodiment, the microchip of this patent may be incorporated into a device for measuring electrochemical or electric signals. This device may be of bench top proportions similar to other devices and analyzers employed in the art, or in a novel and preferred embodiment it may be a portable device, preferably of substantially having reduced size when compared to bench-top devices. Clearly, an advantage of the present technology is the ability to produce accurate and effective analyzers and devices of a reduced size suitable for use at point-of-care sites.

In order to practice the method and employ the device/analyzer of this invention, the inventors are also providing an electrochemical signal detection kit that comprises PCR primers, and one or a plurality of microchip(s) of the invention. The kit may further include PCR reagents other than primers. These kits are optionally included with the sale of the device or analyzer, either the bench-top or the portable variety.

Peptide Nucleic Acid (PNA)-Based Approach

Figure 3:
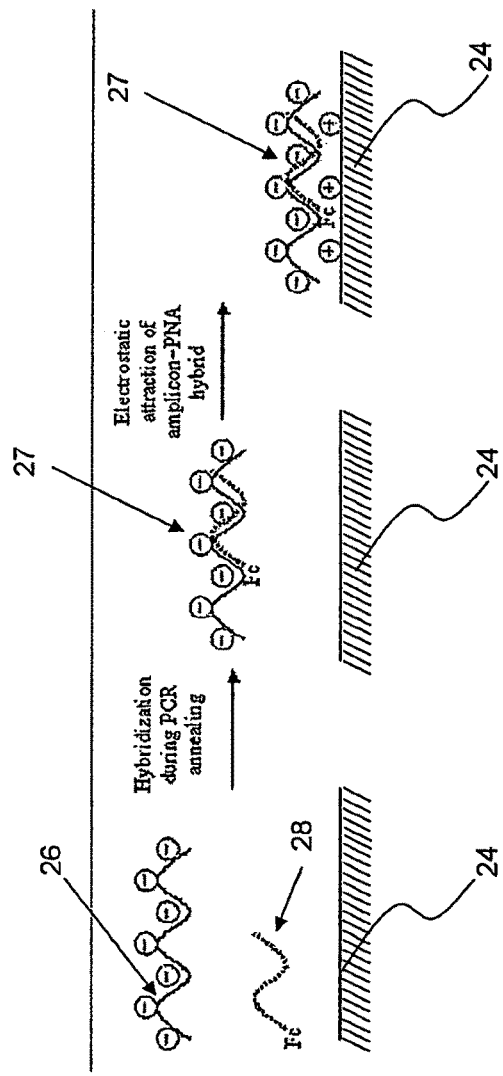
FIG. 3 is an illustration of the method of the invention employing a peptide-nucleic acid (PNA) probe according to one embodiment of the present invention.

In another aspect, this invention provides a peptide nucleic acid- (PNA) probe-based method that takes advantage of the charge neutrality of the probe (in some cases, the probe may be provided with a slight electrically positive charge), and its fast and selective binding, thermostability, and PCR compatibility, as well as the red-ox reversibility of probes such as the ferrocene labeled PNA probe, among others. A working principle of this particular form of the method of the invention is illustrated in FIG. 3 accompanying this patent. In every annealing step of the PCR, the charge neutral or slightly positive ferrocene-PNA (Fc-PNA) probe 28 binds selectively to the negatively charged PCR amplicon 26 along with the PCR primers. At the end of the annealing step, prior to the extension of the primers by the polymerase to generate new amplicon, the amplicon-PNA hybrid 27 is electrostatically attracted to the transducer surface 24 with a potential control. Thus, the ferrocene label of the PNA probe 28 is brought in close proximity with the electrode surface 24 for charge transfer. The electrochemical signal is proportional to the amount of specific amplicon generated during the PCR.

More specifically, this patent provides a second type of real time solution phase method for electrochemically or electrically monitoring or quantifying the amount of nucleic acid(s) by formation of a polymerase chain reaction (PCR) produced polynucleic acid(s) that comprises the following steps:

contacting a sample comprising a target nucleic acid(s) ends, a probe(s) having an electrical charge(s) neutral or positive that is complementary to at least a portion of the target nucleic acid(s), and an electrochemically or electrically conductive labeled marker(s) that is (are) operatively linked to the probe(s) and that when incorporated into the target nucleic acid(s) upon hybridization and subjected to an electric potential produces an intensity change;

applying an electric potential to the sample and detecting or measuring in real time the electric signal(s) produced by the labeled marker(s) incorporated into the target nucleic acid(s); and quantifying the amount of nucleic acid(s) present in the sample and the amount of polynucleic acid(s) produced by correlating the change(s) in signal(s) over time with the formation of polynucleic acid(s).

In a preferred implementation, this method further includes a step for the quantification of the formation of nucleic acid amplification reaction product(s) by calculating a change in signal intensity, wherein any change in the current intensity signal over time indicates the formation of nucleic acid amplification reaction product(s); wherein the intensity change of the electrochemically or electrically conductive labeled marker(s) is proportional to the concentration of the amplification reaction product(s) in the sample. In a more preferred implementation, this method may include running more than one PCR cycle; where the amount of signal(s) change(s) detected and/or measured is (are) proportional to the formation of nucleic acid amplification reaction product(s) in each of said PCR amplification cycles conducted. The signals observed at different points in time show a clear and distinguishable jump for different cycles or groups of cycles of PCR amplification. In another preferred implementation, the electric signal may be detected or measured by placing a conductive electrode(s) in the biological sample.

As in the case with the previously described method and apparatus, device or analyzer, the surface of at least one of the conductive electrode(s) may be formed of or comprise indium tin oxide, gold, platinum, carbon or magnetic particles.

In a preferred implementation, suitable electrochemical labels may comprise one or more of ferrocene or ferrocene derivatives and may suitably be loaded onto a PCR marker such as an oligonucleotide or other molecules comprising them, such as peptide nucleic acid molecules, and others known in the art. One preferred marker comprises a peptide nucleic acid (PNA) molecule(s).

In another preferred implementation, ferrocene-labeled PNA is synthesized with carbodiimide coupling chemistry and comprises the steps of a). dissolving 1-ethyl-3-(3-dimethylaminopropyl) carbodiimide (EDC) in dimethylformamide (DMF)/dimethyl sulfoxide (DMSO) solution;

b). dissolving ferrocene carboxylic acid in the solution of (a);

c). adding amine-group-terminated PNA in the solution of (b) with mixing for overnight; and d). purifying the Fc-DNA products with the aid of HPLC.

Kits similar to the ones described for the earlier method are also contemplated in this patent, and may contain all necessary components for the practice of the invention, such as primers, microchip, electrodes, PCR reagents, and the like. When provided immediately prior to its utilization the kits may also contain a labeled marker(s), and other custom made reagents.

The inventors successfully demonstrated the implementation of the ERT-PCR process in an integrated silicon-glass microchip. Key aspects of optional aspects of the invention, such as electrode surface passivation, effect of potential scanning on the fidelity of the electrochemical detection platform, quantification performance, as well as effects of enzyme and probe concentrations on the signal-to-background ratio are discussed in details. This new and unobvious nucleic acid detection method is far superior to the state-of-the-art fluorescence-based real-time PCR techniques in terms of speed and portability. With the design of multiple working electrodes on a single microchip in one of the embodiments of this invention, this technique is also very promising for real-time multiplexing detection. This invention provides a leap forward in method and device design for the incorporation of functional sample preparation onto a miniaturized device. The present method and device offer a superior technology for application to point-of-care nucleic acid analysis.

The examples presented below are intended to be illustrative of the various methods and compounds of the invention, but not to be limiting the present invention.

EXAMPLES

All general chemicals were obtained from Sigma-Aldrich (St. Louis, Mo.). All PCR reagents were purchased from Invitrogen (Carlsbad, Calif.), unless otherwise stated.

I) Solid Phase Method

Example 1

Preparation of Solid Substrate

Indium tin oxide (ITO)-coated glass (Delta Technologies, Stillwater, Minn.) was first immersed in a solution of $H_2O_2$/$NH_4OH$/$H_2O$ (1:1:5) at 80° C. for 5 minutes. Then, it was rinsed with water and dried with nitrogen gas. The hydrolyzed substrate was treated with a 10% (3-glycidoxypropyl)trimethoxysilane in 95% ethanol for 1 hour. After silanization, the substrate was dried at 50° C. under vacuum.

Example 2

Attachment of Probe to Solid Substrate

A substrate prepared as shown in Example 1 above was incubated with 1 µM of an oligonucleotide probe of sequence:

5'-NH$_2$-TTT TTT TTT TTT TTT TTT TTA AGG AAA CAG CTA TGA C-3' (SEQ. ID NO.1) in phosphate buffer saline (PBS, 100 mM NaCl/10 mM sodium phosphate, pH 7.0) overnight. Excess probes were washed off with PBS. The residual epoxide groups were blocked with ethanolamine for 30 minutes and washed again by PBS.

Example 3

PCR Amplification of Target Nucleic Acid

The PCR master mix contained 1× ThermoPol reaction buffer (20 mM Tris-HCl, 10 mM (NH$_4$)$_2$SO$_4$, 10 mM KCl, 2 mM MgSO$_4$, 0.1% Triton X-100, pH 8.8), 0.2 mM dNTPs (with 0.06 mM dTTP substituted by Fc-dUTP), 0.2 µM forward primer 5'-GTA AAA CGA CGG CCA G-3' (SEQ ID NO.2), 0.2 µM reverse primer 5'-AAG GAA ACA GCT ATG AC-3' (SEQ ID NO.3), 0.02 ng/µL M13mp18 template (Sigma), 0.5 µg/µL. bovine serum albumin, and 0.02 units/µL Vent$_R$® (exo-) DNA polymerase (New England BioLabs, Ipswich, Mass.).

The functionalized ITO chip was dipped into the mixture and subjected to the following thermal cycling profile:
 initial denaturation at 95° C. for 2 minutes;
 25 cycles at 95° C. for 20 seconds, at 55° C. for 20 seconds, and at 72° C. for 10 seconds.

Example 4

Synthesis of Ferrocene-dUTP Labeled Marker

Fc-dUTP was synthesized according to the King et al. protocol (Wlassoff, W. A.; King, G. C., Nucleic Acids Res. 2002, 30, e58), with minor modification on the purification procedure to improve the yield. After certain PCR cycles, the ITO-coated chip was removed from the PCR tube and rinsed with water.

Differential pulse voltammetric measurements were performed using Autolab PGSTAT30 (Eco Chemie, The Netherlands) with a pulse amplitude of 100 mV and scan rate of 25 mV/s. Pt was used as the counter and pseudo-reference electrodes.

The thermal control system for the PCR consisted of a data acquisition card (PCI-MIO-16E-1, National Instruments, Austin, Tex.) along with a signal conditioning board (SC-2042-RTD, National Instruments) connected to the temperature sensors.

A digital feedback proportional-integral-derivative (PID) control algorithm was implemented in LabVIEW software (National Instruments) to control voltage supply to the heater by a power source (HP6629A, Hewlett-Packard, Rockville, Md.).

Electrochemical measurements were performed with an Autolab PGSTAT30 potentiostat/galvanostat (Eco Chemie, The Netherlands) controlled by the General Purpose Electrochemical System (GPES) software (Eco Chemie).

Example 5

Fabrication of Silicon-Glass Microchip

Figure 4A:
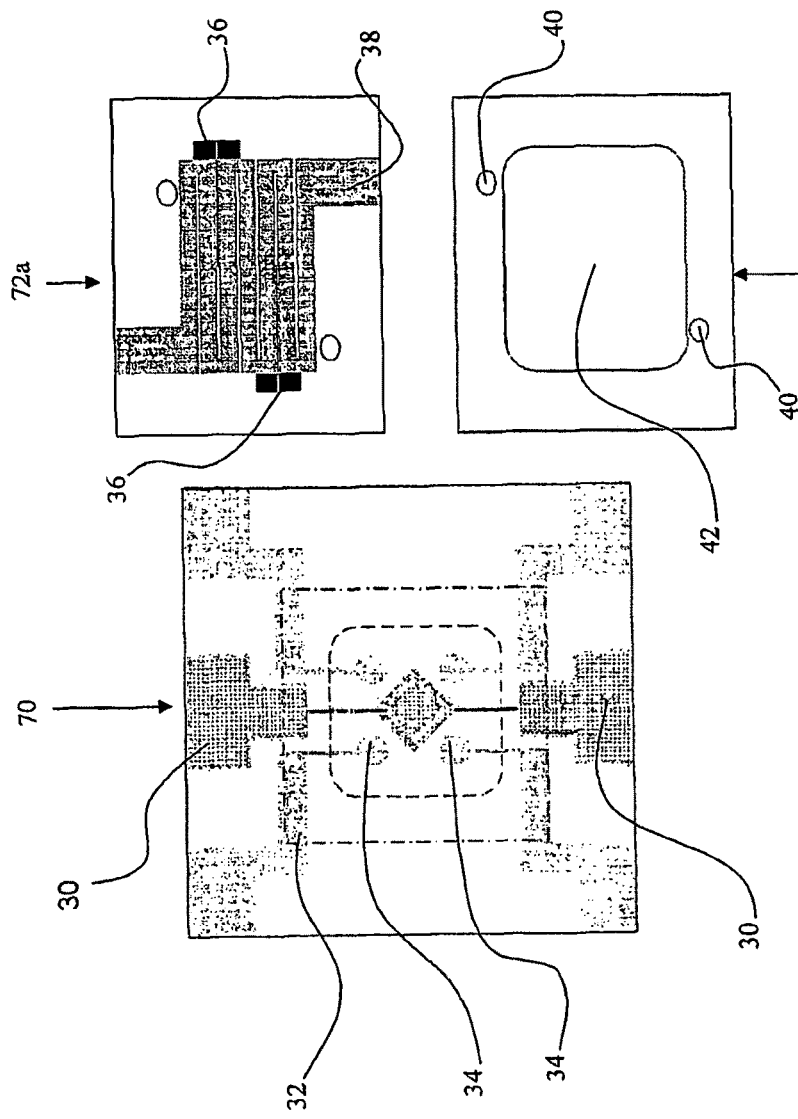
FIG. 4 is a schematic diagram showing (A) the layout of the silicon and glass substrates; (B) initial state of the oligonucleotide capture probe modified ITO electrode prior to the PCR; and (C) the final extended capture probe at the end of the PCR according to one embodiment of the present invention.
Figures 4B, 4C:
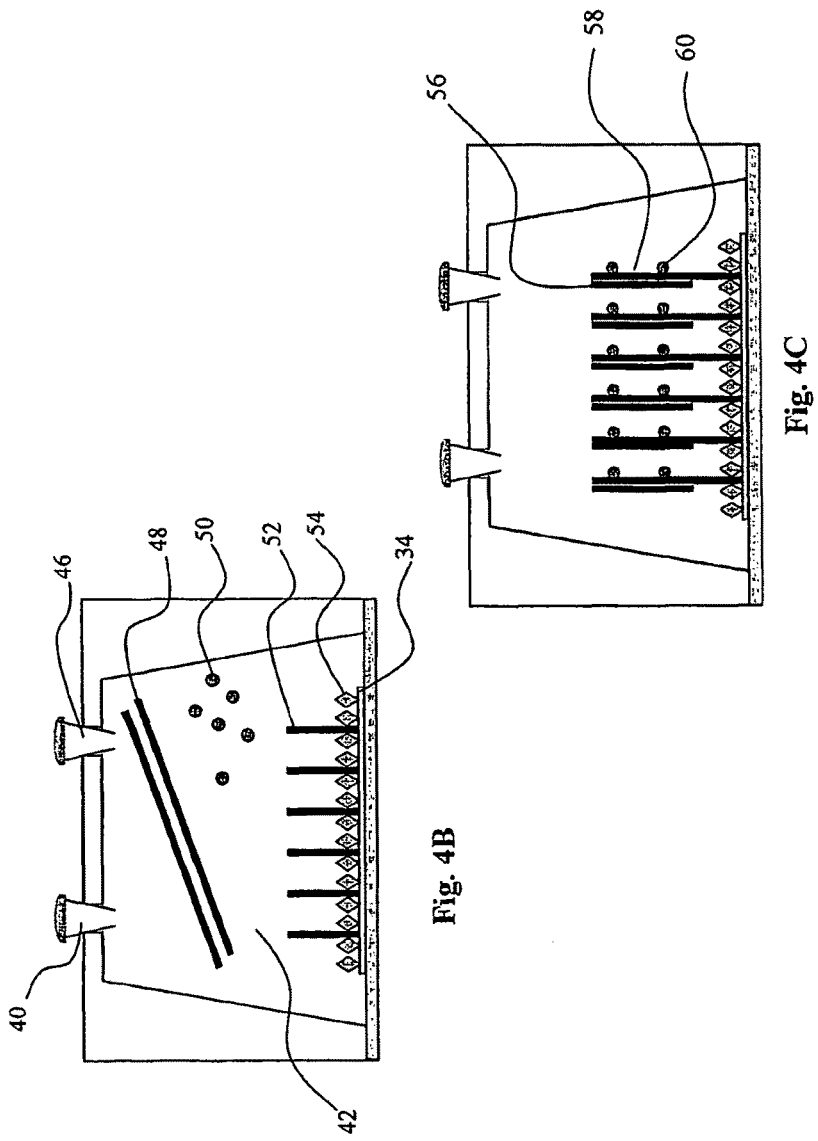

An integrated silicon-glass microchip consisted of silicon (Si) (thickness of 400 µm) and ITO-coated glass substrates (Delta Technologies, Stillwater, Minn.) with metallic patterns and microstructures. See, FIGS. 4A, 4B, and 4C provided with this patent.

Thin film platinum (Pt) heaters 38 and temperature sensors 36 (thickness of 100 nm) were patterned on the front side of the Si chip 72a, for PCR thermal cycling and the microreactor 42 (length and width of 5 mm, depth of 325 µm) for DNA amplification, etched by the inductively coupled plasma-deep reactive ion etching (ICP-DRIE) process, was located on the back of the Si chip 72b. ICP-DRIE etched feed holes 40 (diameter of 500 µm, depth of 100 µm) on the back side of the Si chip 72b were used for the injection and removal of PCR solution.

The ITO-coated glass chip 70 had thin film Pt pseudo-reference and counter electrodes 30 (thickness of 100 nm) on the center surrounded by four ITO-based (thickness of 100 nm) circular working electrodes 34 for probe immobilization and solid-phase extension of the oligonucleotide capture probe.

Ultra-violet (UV) curing optical cement (Type UV-69, Summers Optical, Hatfield, Pa.) was used to seal the silicon 72 and glass chips 70 (with the silicon chip 72 being placed on the glass chip 70 at the location 32) and the curing procedure was done according to the manufacturer's instruction, and obtained as similarly reported by the inventors previously for the multiplexed detection of *Escherichia coli* and *Bacillus subtilis*. See, Yeung, S. W.; Lee, T. M. H.; Cai, H.; Hsing, I. M. Nucleic Acids Res. 2006, 34, e118.

Example 6

Probe Immobilization and Electrode Passivation

Prior to the UV bonding, the patterned glass substrates were sequentially sonicated in an Alconox solution (8 g of Alconox per liter of water), propan-2-ol, and twice in water, with each sonication lasting for 15 minutes. Then, they were dried with nitrogen gas and treated in a plasma cleaner (Harrick Plasma, Ithaca, N.Y.) for 10 minutes.

The hydrolyzed glass substrates then were immersed in a 10% (3-glycidoxypropyl)trimethoxysilane (dissolved with 95% ethanol) for 1 hour. The silanized substrates were dried at 50° C. under vacuum for 3 hours and bonded with the silicon substrate. After the UV bonding, a 1 µM oligonucleotide probe solution of sequence: 5'-NH$_2$-TTT TTT TTT TTT TTT TTT TTA AGG AAA CAG CTA TGA C-3' (SEQ. ID NO.1) in phosphate buffered saline (PBS, 100 mM NaCl/10 mM sodium phosphate, pH 7.0) was introduced into the microchamber and incubated overnight. Excess probes were washed off with PBS. Residual epoxide groups were blocked with ethanolamine for 12 hours, unless otherwise stated.

Finally, the microchamber was flushed thoroughly with autoclaved double-deionized water and dried with nitrogen gas.

Example 7

Example of Electrochemical Real-Time PCR Method

The PCR master mix contained 1× ThermoPol reaction buffer (20 mM Tris-HCl, 10 mM (NH$_4$)$_2$SO$_4$, 10 mM KCl, 2 mM MgSO$_4$, 0.1% Triton X-100, pH 8.8), 0.2 mM dNTPs (with 0.06 mM dTTP substituted by Fc-dUTP), 0.2 µM forward primer 5'-GTA AAA CGA CGG CCA G-3' (SEQ ID NO:2), 0.2 µM reverse primer 5'-AAG GAA ACA GCT ATG AC-3' (SEQ ID NO.3), 0.04 ng/µL M13mp18 template, 0.5 µg/µL bovine serum albumin, and 0.04 units/pt Vent$_R$® (exo-) DNA polymerase (New England BioLabs, Ipswich, Mass.).

Referring to FIGS. 4B and 4C, the master mix was pipetted into the microchamber, 42 and the injection holes 40 were sealed with Bostik's Blu-Tack. The chip was subjected to the following thermal cycling profile: initial denaturation at 94° C. for 2 minutes; 30 cycles at 94° C. for 20 seconds; at 55° C. for 20 seconds; 72° C. for 10 seconds. Apart from on-chip thermal control by the patterned heater 38 (shown in FIG. 4A) and temperature sensors 36 (shown in FIG. 4A), the PCR thermal cycling of the microchip could also be done by the conventional cycler (Eppendorf® Mastercycler® personal) with very similar results (data not shown). Differential pulse voltammetric measurements were performed with pulse amplitude of 100 mV and scan rate of 25 mV/s.

Example 8

Results

A schematic of the electrochemical real-time PCR (ERT-PCR) method conducted on a silicon-glass microchip is shown in FIGS. 4B and 4C of this patent. It is important for the successful implementation of on-chip ERT-PCR to make successful readings of accumulative electrochemical signal produced by the increased amount of PCR amplicon at each PCR thermal cycle.

This method is unlike the ERT-PCR conducted in an Eppendorf® tube PCR process. See, Yeung, S. W.; Lee, T. M. H.; Hsing, I. M. J. Am. Chem. Soc. 2006, 128, 13374-13375. This on-chip ERT-PCR process involves oligonucleotide extension of solution- and solid-phases in a closed microenvironment, and repetitive electrochemical potential scanning without removal of solution and surface-adsorbed impurities. Several crucial factors, e.g. passivation of the sensing electrode, strategy on the electrochemical scanning, and control of enzyme and oligo probe concentrations, that would greatly affect the analytical signal of this new assay platform are discussed in the following paragraphs.

Electrode Surface Passivation

Figure 5:
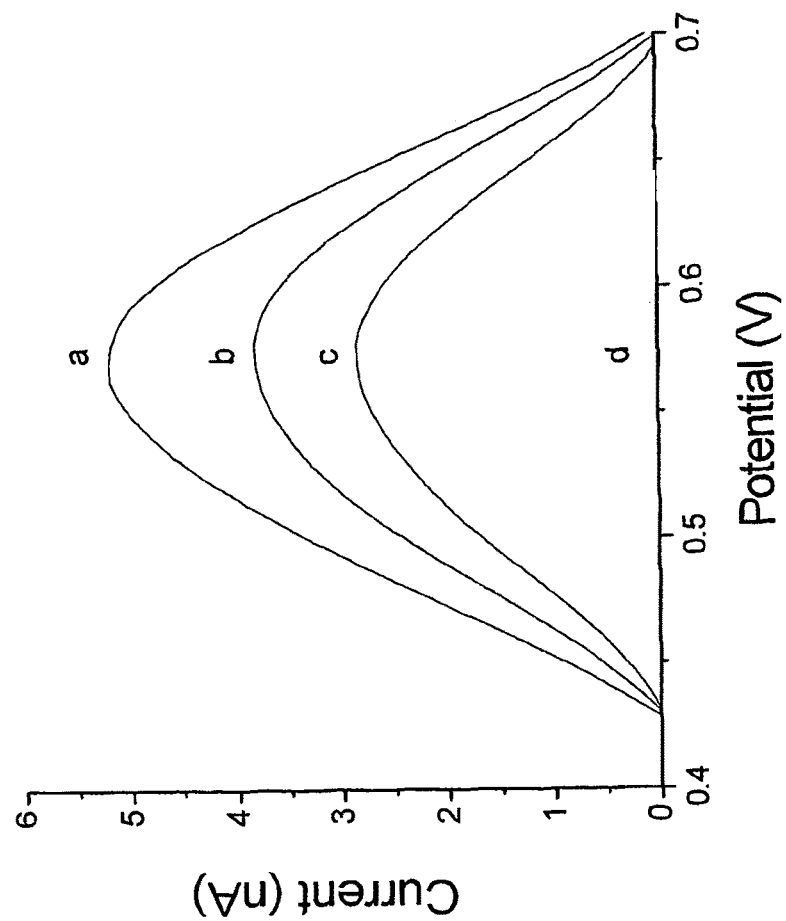
FIG. 5 is a differential pulse voltammetric scan of the ITO electrodes in the absence of the template according to the same embodiment of the present invention. The chips were incubated with ethanolamine for different times: (a) 1 hour; (b) 2 hours; (c) 3 hours; and (d) 12 hours. Electrochemical measurements were carried out using a pulse amplitude of 100 mV/s and a scan rate of 25 mV/s. The background signals were obtained at the end of 30-cycle PCRs.

One of the biggest challenges in running ERT-PCR in a microchip format is to minimize, if not totally eliminate, the background signal caused by the solution-phase Fc-dUTP. FIG. 5 shows that the background signal is strongly dependent on the duration of the ethanolamine blocking step. Characteristic redox peaks from Fc-dUTP 50 (shown in FIG. 4B) (~0.57 V vs. Pt pseudo reference electrode) are noticeable with blocking time shorter than 3 hours (curve c on FIG. 5), which is likely caused by the nonspecific adsorption of the Fc-dUTP 50 to the unreacted epoxide groups and/or free diffusion of the Fc-dUTP 50 to the ITO surface 34 (shown in FIG. 4B). For a long enough blocking time, i.e., 12 hours (curve d on FIG. 5), the baseline is nearly flat. This implies that almost all the residual epoxide groups are reacted with the ethanolamine so that nonspecific adsorption and diffusional access of the Fc-dUTP 50 to the electrode surface 34 is minimized. With this, the signal-to-noise ratio is significantly increased and hence a lower detection limit is expected. When practicing this method, no washing step is required to remove the free soluble markers from the solution and the method, therefore, achieves real-time PCR quantification.

Electrode Scanning

The method described herein is different from the fluorescence-based real-time PCR, ERT-PCR methods. The present method requires electrochemical scanning during or at intermittent interval during the thermal cycling process in order to "electrochemically" monitor the amplification into PCR products in a "real-time" setting. In one of the embodiments, there are four circular ITO-based electrodes 34 patterned in our silicon-glass microchip 70. See, FIG. 4A showing this patent.

It is desirable to have each electrode scanned for a plurality of times, e.g. once for every PCR cycle and 30 times in a 30 cycle PCR, without affecting the PCR performance. However, in fact the adsorption characteristics of a charged species, e.g. dNTPs, $Mg^{2+}$, and of the polymerase enzyme may change when exposed to repetitive potential scanning, a subtle change that might affect the nucleotide extension on the solid electrode surface.

To investigate the effect of electrochemical scanning, the ERT-PCR process was performed on microchips with all the ITO electrodes being immobilized with the same capture oligonucleotide probes. In one set of the microchips, all four ITO electrodes were electrochemically scanned for multiple times per every five cycles; while in the other chips, the four ITO electrodes were selectively and singly scanned at the thermal cycle of 0th, 10th, 20th and 30th, respectively.

Superiority Over Fluorescent-Based Method

Figures 6A, 6B:
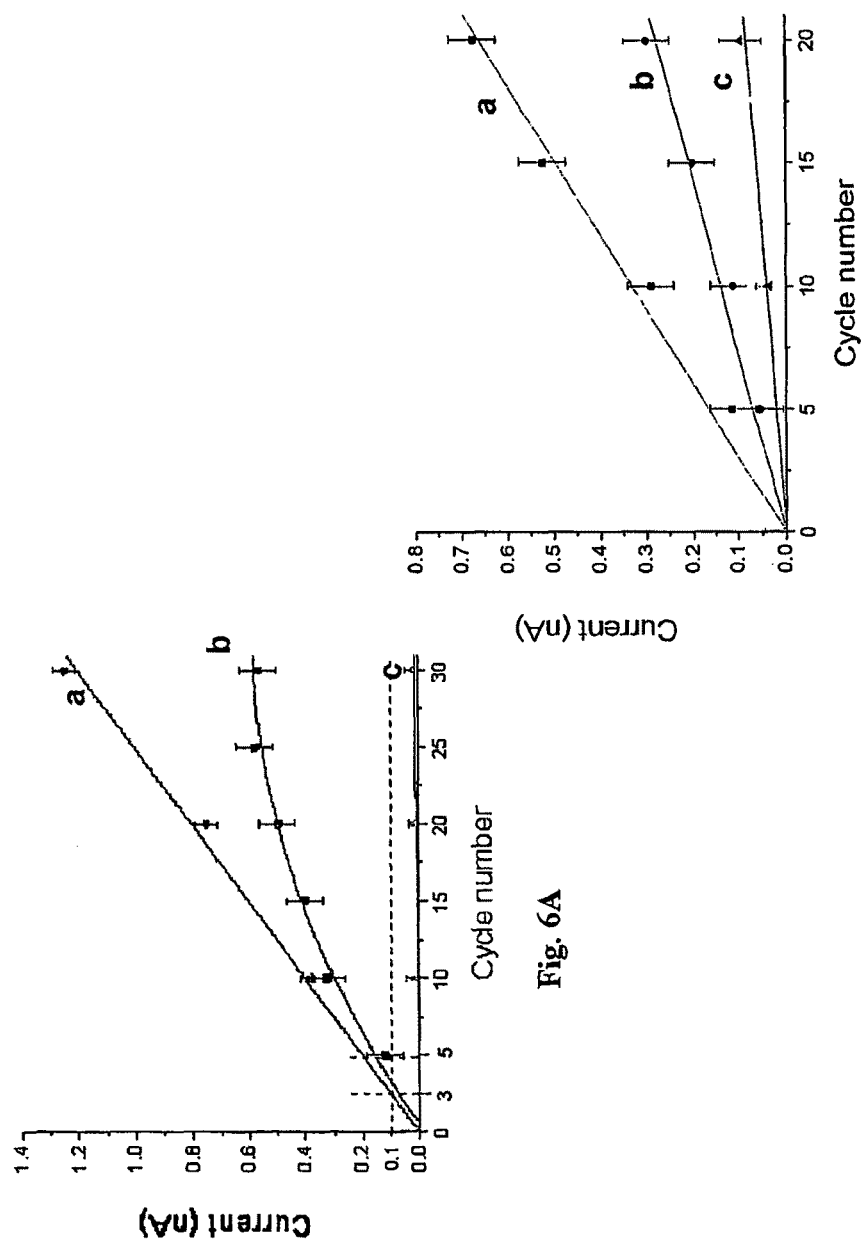
FIG. 6A shows a plot of peak current signal in a differential pulse voltammetric scans against PCR cycle number with different electrode scanning strategies according to the same embodiment of the present invention. (a) ● Single-scan in the presence of template ($3 \times 10^6$ copies/$\mu$L); (b) ■ multiple-scan in the presence of template ($3 \times 10^6$ copies/$\mu$L); and (c) ▲ single-scan in the absence of template.
FIG. 6B shows a plot of current signal against PCR cycle number in the presence of target DNA template ($3 \times 10^3$ copies/$\mu$L) at different Vent polymerase concentrations according to one embodiment of the present invention. (a) ■ 0.32 units/$\mu$L; (b) ● 0.24 units/$\mu$L; and (c) ▲ 0.04 units/$\mu$L.
Figure 6C:
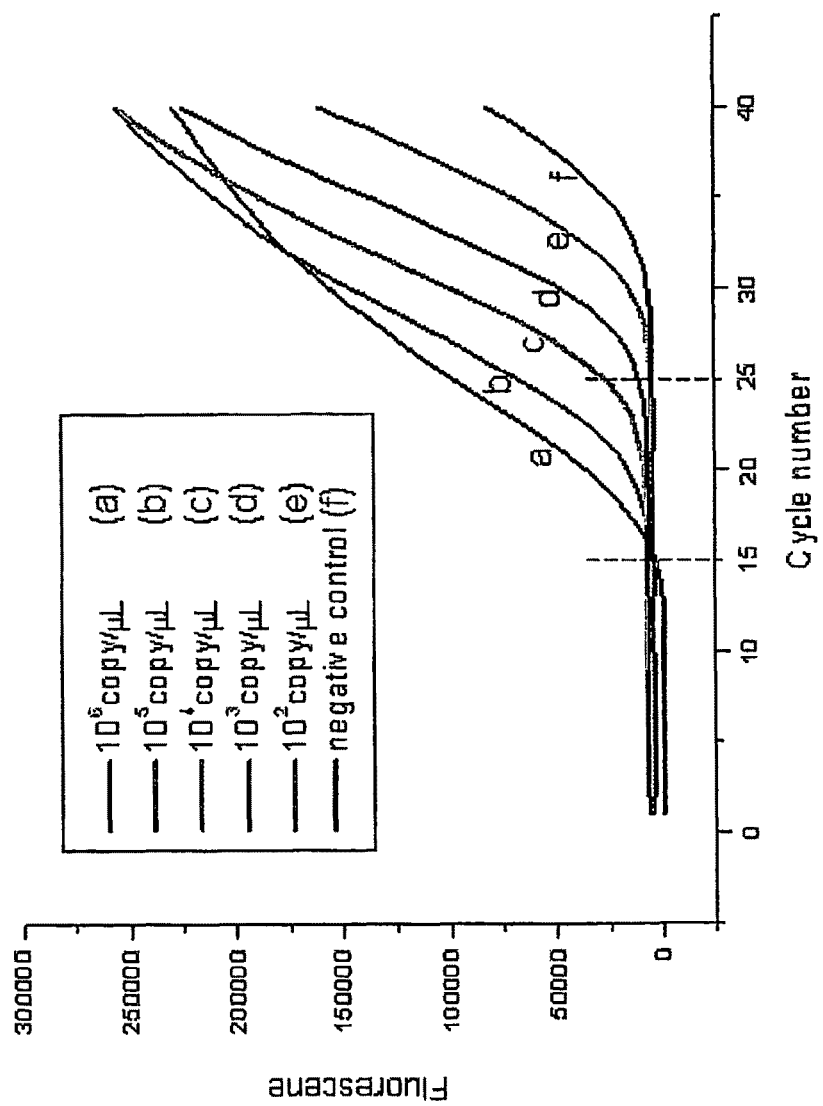
FIG. 6C shows a plot of fluorescent signal (SYBR Green assay) against PCR cycle number for a series of dilutions from $10^2$ to $10^6$ DNA copies/$\mu$L. (a) $10^6$ copy/$\mu$L; (b) $10^5$ copy/$\mu$L; (c) $10^4$ copy/$\mu$L; (d) $10^3$ copy/$\mu$L; (e) $10^2$ copy/$\mu$L; (f) negative control.

As may be seen from FIG. 6A, a cycle-by-cycle increase of the electrochemical signal was obtained, indicating a successful incorporation of the Fc-dUTP redox marker on the extended probe. A low background noise for the amplification case without DNA template (curve c of FIG. 6A) suggests effective minimization of the unspecific electrochemical interference. With an initial template concentration of $3\times10^6$ copies/µL, the "onset" cycle number at which the analytical signal in ERT-PCR (~3-5 cycles) is distinguishable from the background signal is much smaller than that for the fluorescence-based real-time PCR counterparts (usually 15-25 cycles). See FIGS. 6A and 6C for comparison. This suggests that fewer PCR cycles are needed for the ERT-PCR technique. It should be noted that fluorescence-based methods are known to detect a very low template concentration. The present strategy for reducing the required initial template concentration is discussed below.

The leveling-off gain of the electrochemical signal at high cycle numbers (data points in squares, curve b of FIG. 6A) on the multiply-scanned electrode is a clear indication that the multiple electrochemical scanning indeed may have an adverse effect to the process as compared to the signal measured on the single scanning electrode (data points in circle, curve a of FIG. 6A). Actually, similar plots of signal saturation at high cycle numbers were also observed when employing a fluorescence-based real-time PCR method of signal measurement.

However, the reasons associated with signal saturation in these two methods are very likely of a very different nature. In the fluorescence-based method, the phenomena may be attributed to the depletion of limiting reagents, while in the present ERT-PCR method, it is most likely associated with electrochemical scanning itself although the actual mechanism of the potential scanning is not yet fully understood. Nevertheless, the experimental results strongly suggest that the effect of multiple scanning may be reduced by adding more polymerase (data not shown). One possibility to explain these results is that irreversible adsorption of enzyme and other species on the electrode may play a role in the process.

Although multiple scanning may have an impact on the on-chip ERT-PCR process, it is possible to avoid it by having more ITO-based working electrodes in the microchip and/or using each of the electrodes for a single scanning purpose at a specific thermal cycle(s). The linear relationship of the signal and the cycle number in the single-scanning measurement (curve a, FIG. 6A) reflects this strategy. See, for example FIG. 6A of this patent. Therefore, the experimental data presented in the remaining Examples were obtained based on a single-scanning electrode. Actually, density of the immobilized probe on the electrode may also affect the electrochemical signal in ERT-PCR process, the implications of which are discussed in later paragraphs.

Calibration Plot

Figure 7A:
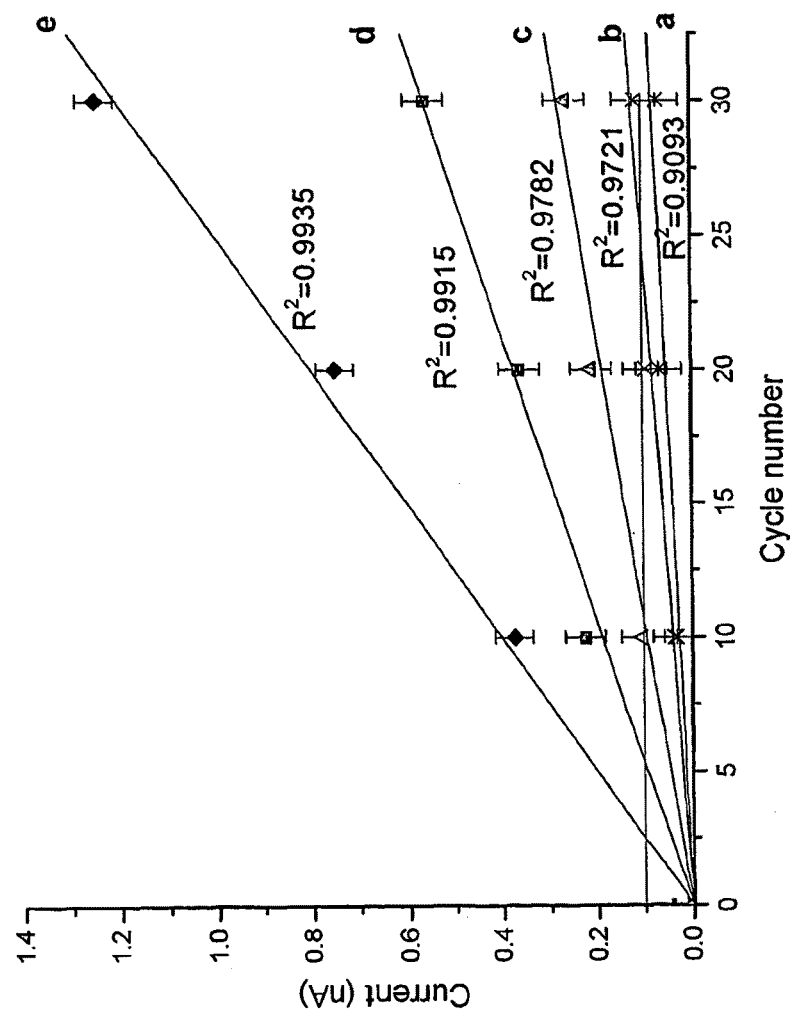
FIG. 7A shows a plot of peak current signal against PCR cycle number for a series of dilutions from $10^2$ to $10^6$ DNA copies/$\mu$L. (a) * $3 \times 10^2$; (b) × $3 \times 10^3$; (c) ▲ $3 \times 10^4$; (d) ■ $3 \times 10^5$; (e) ♦ $3 \times 10^6$ according to one embodiment of the present invention.
Figure 7B:
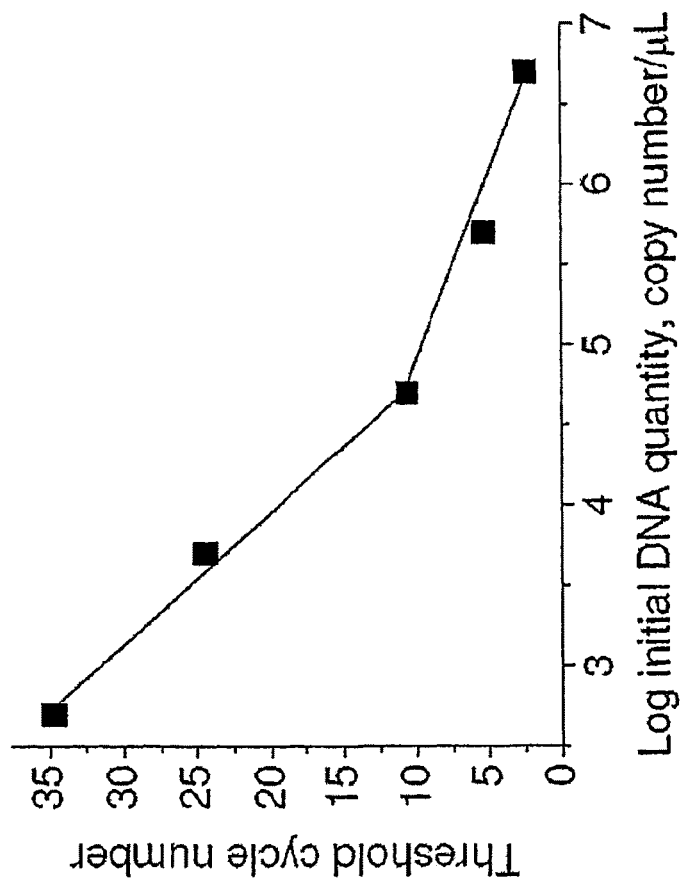
FIG. 7B is a standard curve with a threshold set at 0.1 nA according to the same embodiment.

For any real-time PCR technique, it is important to evaluate its performance in the quantification of target DNA molecules (target nucleic acids). In the ERT-PCR method of the invention, the standard curves as shown in the FIG. 7B were obtained by setting the threshold value at 0.1 nA for the current-cycle number plots with different initial template concentrations. Rather than the linear calibration plot required by fluorescence-based real-time PCR methods, the electrochemical calibration plot may be approximated by doing two linear regimes, with a crossover point at about $10^5$ copies/4. See, for instance FIG. 7B of this patent. It should be noted that the electrochemical real-time PCR method provides a superior performance, e.g. in terms of the threshold cycle number, than the state-of-the-art fluorescence-based real-time PCR method at high template concentrations (>$10^5$ copies/µL).

Referring back to FIG. 7A, for template concentrations lower than $10^4$ copies/µL (curves a and b), the threshold cycle number of the present electrochemical method exceeds that of any fluorescence-based methods, possibly due to competition between the solution phase primer and the immobilized probe for the target amplicon. At low target copy number, the solution phase primer tends to dominate during the annealing step. Hence, it may be necessary to build up sufficient amount of PCR products (polynucleic acids) to facilitate solid phase probe extension, which may lead to a need for a large threshold cycle number in cases of low initial DNA (target nucleic acid) sample content.

Effects of Enzyme and Probe Concentrations on Peak Current Signals

As already discussed, the PCR threshold cycle number required for low template concentration samples is likely higher. In the fluorescence-based methods, little may be done to increase the signal-to-background ratio given that background fluorescence is not easily eliminated. On the other hand, the enzyme and probe concentrations may be used to enhance the sensitivity of the ERT-PCR method of the invention. FIG. 6B provided with this patent shows that the analytical signals may be greatly increased by increasing enzyme concentrations (without increase in the background signals, data not shown). An increase of 8 times in the enzyme concentration produces an 8-fold increase in the analytical signal. More importantly, at initial template concentrations of $3\times10^3$ copies/µL, the threshold cycle number is reduced from 25 to less than 5.

Figure 8:
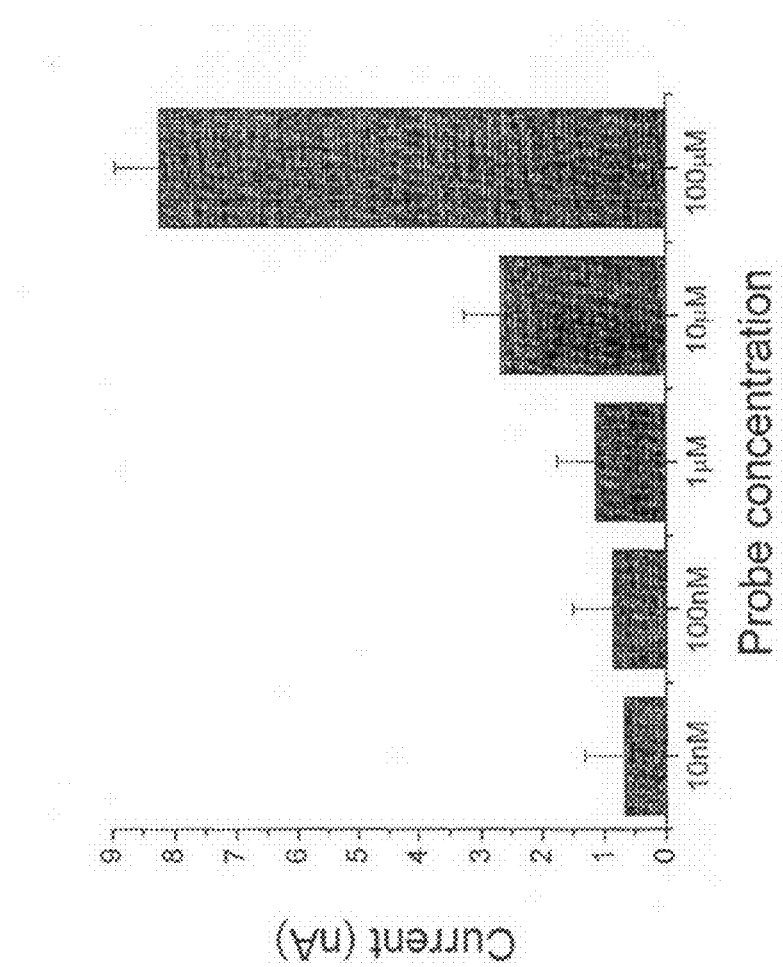
FIG. 8 shows a plot of peak current signal after 30-cycle PCR against probe concentration according to one embodiment of the present invention. The probe concentration ranges from 10 nM to 100 $\mu$M in the probe immobilization step, with the initial template concentration being $3 \times 10^6$ copies/$\mu$L.

Another way to improve the signal-to-background ratio may be achieved by using a higher probe concentration during the immobilization step. See, FIG. 8 of this patent. The probe concentration during the immobilization step for all previous experiments is 1 µM. When the concentration is raised to 100 µM, the analytical signal increases by a factor of 8.

II) Solution Phase Method

Example 9

Chip Fabrication and Preparation

The biochips used in the solution phase method were prepared according to the method described in Example 1 above.

Example 10

Solution Preparation

The PCR master mix contained 1× ThermoPol reaction buffer (20 mM Tris-HCl, 10 mM $(NH_4)_2SO_4$, 10 mM KCl, 2 mM $MgSO_4$, 0.1% Triton X-100, pH 8.8), 0.2 mM dNTPs (with 0.06 mM dTTP substituted by Fc-dUTP), 0.2 µM forward primer 5'-GTA AAA CGA CGG CCA G-3' (SEQ. ID NO.4), 0.2 µM reverse primer 5'-AAG GAA ACA GCT ATG AC-3' (SEQ. ID NO.5), 0.2 µM Fc-PNA-probe 5'-Fc-TAG AGT CGA CCT GCA GGC ATG C-3' (SEQ. ID NO.6), 0.04 ng/µL M13mp18 template, 0.5 µg/µL bovine serum albumin, and 0.04 units/µL. $Vent_R$® (exo-) DNA polymerase (New England BioLabs, Ipswich, Mass.).

Example 11

Electrochemical Real-Time PCR

The master mix was pipetted into the microchamber, with the injection holes being sealed with Bostik's Blu-Tack, and subjected to the following thermal cycling profile: initial denaturation at 94° C. for 2 minutes; 30 cycles at 94° C. for 20 seconds (denaturation); at 55° C. for 20 seconds (annealing); 25° C. for 60 seconds (measurement); and 72° C. for 10 seconds (extension). During the measurement step, a positive potential was applied (i.e. +0.5V versus Pt/Pt reference/counter electrodes for 20~30 seconds) and then a differential pulse voltammetric Measurement was performed with a pulse amplitude of 100 mV and scan rate of 25 mV/s. Finally, a negative potential was applied to release the attached PCR amplicons/primers/probe hybrids back to the solution for extension.

The preferred embodiments of the present invention as well as various examples thereof, are thus fully described. Although the description referred to particular embodiments, it will be clear to one skilled in the art that the present invention may be practiced with variation of these specific details. Hence this invention should not be construed as limited to the embodiments set forth herein.

For instance, an alternative implementation to the solid phase method may be feasible in which the probe, instead of comprising a sequence complementary to the target nuclear acid, may comprise an immobilization unit being operationally coupled to the first primer by sequence complementarity with the first primer. Consequently, the first primer is then associated with or bound to the solid surface through its interaction with the immobilization unit.

REFERENCES (1) Wilhelm, J.; Pingoud, A. *ChemBioChem* 2003, 4, 1120-1128.
(2) Drummond, T. G.; Hill, M. G.; Barton, J. K. *Nature Biotech.* 2003, 21, 1192-1199.
(3) Kerman, K.; Kobayashi, M.; Tamiya, E. *Meas. Sci. Technol.* 2004, 15, R1-R11.
(4) Gooding, J., Justin *Electroanalysis* 2002, 14, 1149-1156.
(5) Wang, J. *Anal. Chim. Acta* 2002, 469, 63-71.
(6) Lai, R. Y.; Lagally, E. T.; Lee, S. H.; Soh, H. T.; Plaxco, K. W.; Heeger, A. J. *PNAS* 2006, 103, 4017-4021.

(7) Lee, T. M. H.; Hsing, I. M. *Anal. Chem.* 2002, 74, 5057-5062.
(8) Lee, T. M. H.; Caries, M. C.; Hsing, I. M. *Lab Chip* 2003, 3, 100-105.
(10) Liu, R. H.; Yang, J.; Lenigk, R.; Bonanno, J.; Grodzinski, P. *Anal. Chem.* 2004, 76, 1824-1831.
(12) Adessi, C.; Matton, G.; Ayala, G.; Turcatti, G.; Mermod, J. J.; Mayer, P.; Kawashima, E. *Nucleic Acids Res.* 2000, 28, e87.
(13) Carmon, A.; Vision, T. J.; Mitchell, S. E.; Thannhauser, T. W.; Muller, U.; Kresovich, S. *Bio Techniques* 2002, 32, 410-420.

What is claimed is:

1. A real time solid phase method for electrochemically or electrically monitoring or quantifying the amount of nucleic acid(s) by formation of a polymerase chain reaction (PCR) produced polynucleic acid(s) comprising contacting a sample comprising a target nucleic acid(s), a solid surface bound probe(s) comprising a first primer(s) provided with a sequence(s) that is complementary to at least a portion of one end of the target nucleic acid(s), a second primer(s) in solution that is complementary to at least a portion of the opposing end of the complementary strand of the target nucleic acid(s), and an electrochemically or electrically conductive labeled marker(s) that is(are) adapted for incorporation into a polynucleic acid(s) by chain polymerization and when incorporated thereof produces a signal(s) change(s) if subjected to an electric potential wherein at least one of the probe(s) is(are) bound onto the conductive electrode surface and said probes remain immobilized during chain polymerization;

adding a polymerase chain reaction enzyme(s) under conditions effective for PCR amplification to occur;

applying an electric potential to the sample and detecting or measuring in real time an electric signal(s) produced by the labeled marker(s) incorporated into said solid surface bound probe(s); and quantifying the amount of nucleic acid(s) present in the sample and the amount of polynucleic acid(s) produced by correlating the change(s) in signal(s) over time with the formation of polynucleic acid(s), wherein said electric signal(s) is detected or measured with a conductive electrode(s) placed in the sample; said electrode(s) is(are) treated for a sufficient period of time to prevent electron transfer from said un-reacted electrochemically or electronically conductive labeled marker during real time solid phase PCR;

wherein said electrodes are treated with a blocking agent for at least twelve hours; and said blocking agent of said treatment is ethanolamine.

2. The method of claim 1, further comprising denaturing the target nucleic acid(s) prior to the polymerization reaction; and wherein the polymerase chain reaction enzyme comprises a thermo-stable enzyme.

3. The method of claim 1, wherein the signal(s) change comprise(s) an intensity change(s) that is proportional to the concentration of the polynucleic acid(s) produced, and of nucleic acid(s) in the sample.

4. The method of claim 1, further comprising conducting more than one PCR amplification cycles; wherein each signal(s) change(s) is(are) proportional to the formation of polynucleic add(s) in each PCR amplification cycle.

5. The method of claim 1 wherein a surface of at least one of the conductive electrode(s) comprises indium tin oxide, gold, platinum, carbon or magnetic particles.

6. The method of claim 1, where in the label(s) comprise(s) ferrocene or ferrocene derivatives.

7. The method of claim 1, wherein the marker(s) comprise(s) dUTP, dATP, dGTP, or dCTP.

\* \* \* \* \*

SEQUENCE LISTING

<160> NUMBER OF SEQ ID NOS: 6

<210> SEQ ID NO 1
<211> LENGTH: 37
<212> TYPE: DNA
<213> ORGANISM: Artificial
<220> FEATURE:
<223> OTHER INFORMATION: probe sequence

<400> SEQUENCE: 1
tttttttttt tttttttttt aaggaaacag ctatgac            37

<210> SEQ ID NO 2
<211> LENGTH: 16
<212> TYPE: DNA
<213> ORGANISM: Artificial
<220> FEATURE:
<223> OTHER INFORMATION: forward primer

<400> SEQUENCE: 2
gtaaaacgac ggccag                                    16

<210> SEQ ID NO 3
<211> LENGTH: 17
<212> TYPE: DNA
<213> ORGANISM: Artificial
<220> FEATURE:
<223> OTHER INFORMATION: reverse primer

<400> SEQUENCE: 3
aaggaaacag ctatgac                                   17

<210> SEQ ID NO 4
<211> LENGTH: 16
<212> TYPE: DNA
<213> ORGANISM: Artificial
<220> FEATURE:
<223> OTHER INFORMATION: forward primer

<400> SEQUENCE: 4
gtaaaacgac ggccag                                    16

<210> SEQ ID NO 5
<211> LENGTH: 17
<212> TYPE: DNA
<213> ORGANISM: Artificial
<220> FEATURE:
<223> OTHER INFORMATION: reverse primer

<400> SEQUENCE: 5
aaggaaacag ctatgac                                   17

<210> SEQ ID NO 6
<211> LENGTH: 22
<212> TYPE: DNA
<213> ORGANISM: Artificial
<220> FEATURE:
<223> OTHER INFORMATION: Fc-PNA-probe

```
<400> SEQUENCE: 6
tagagtcgac ctgcaggcat gc                                          22
```